United States Patent
Low et al.

(10) Patent No.: US 11,734,839 B2
(45) Date of Patent: Aug. 22, 2023

(54) APPARATUS AND METHOD FOR REMOVING BREATHING MOTION ARTIFACTS IN CT SCANS

(71) Applicant: THE REGENTS OF THE UNIVERSITY OF CALIFORNIA, Oakland, CA (US)

(72) Inventors: Daniel Low, Los Angeles, CA (US); Anand Santhanam, Culver City, CA (US); Dylan O'Connell, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 507 days.

(21) Appl. No.: 17/027,294

(22) Filed: Sep. 21, 2020

(65) Prior Publication Data

US 2021/0074007 A1 Mar. 11, 2021

Related U.S. Application Data

(63) Continuation of application No. PCT/US2019/023706, filed on Mar. 22, 2019.

(Continued)

(51) Int. Cl.
*G06T 7/246* (2017.01)
*G16H 30/20* (2018.01)
*G16H 30/40* (2018.01)

(52) U.S. Cl.
CPC ............ *G06T 7/251* (2017.01); *G06T 7/248* (2017.01); *G16H 30/20* (2018.01); *G16H 30/40* (2018.01); *G06T 2207/10081* (2013.01)

(58) Field of Classification Search
CPC .................. G06T 7/251; G06T 7/248; G06T 2207/10081; G06T 2211/412;
(Continued)

(56) References Cited

U.S. PATENT DOCUMENTS 7,085,342 B2 * 8/2006 Younis .................. G06T 11/005
378/4
8,600,132 B2 * 12/2013 Razifar ................ A61B 6/4417
382/128
(Continued)

FOREIGN PATENT DOCUMENTS

WO 2019183562 A1 9/2019

OTHER PUBLICATIONS

McClelland, Jamie R., et al., "A generalized framework unifying image registration and respiratory motion models and incorporating image reconstruction, for partial image data or full images", Open Access IOP Publishing, Institute of Physics and Engineering in Medicine, Phys. Med. Biol. 62, (2017), pp. 4273-4292.

(Continued)

*Primary Examiner* — Molly Wilburn
(74) *Attorney, Agent, or Firm* — O'Banion & Ritchey LLP; John P. O'Banion

(57) ABSTRACT

A method and apparatus for removing breathing motion artifacts in imaging CT scans is disclosed. The method acquires raw imaging data from a CT scanner, and processes the raw CT imaging data by removing motion-induced artifacts via a motion model. Processing the imaging data may be achieved by initially estimating a 3D image to provide an estimate of raw sinogram image data, comparing the estimate to an actual CT sinogram, determining a difference between the sinograms, and iteratively reconstructing the 3D image by using the difference to alter the 3D (Continued)

image until the sinograms agree, wherein the 3D image moves according to the motion model.

29 Claims, 3 Drawing Sheets

Related U.S. Application Data

(60) Provisional application No. 62/646,968, filed on Mar. 23, 2018.

(58) Field of Classification Search
CPC . G06T 2211/424; G06T 11/006; G16H 30/20; G16H 30/40; A61B 6/5205; A61B 6/5264; A61B 6/032
See application file for complete search history.

(56) References Cited

U.S. PATENT DOCUMENTS

| | | | |
|---|---|---|---|
| 9,269,166 B2* | 2/2016 | Hansis | G06T 7/0012 |
| 10,398,382 B2* | 9/2019 | Sanders, III | A61B 6/5205 |
| 2009/0110238 A1 | 4/2009 | Li | |
| 2009/0180589 A1 | 7/2009 | Wang | |
| 2010/0310140 A1* | 12/2010 | Schneider | G06T 7/277 |
| | | | 382/128 |
| 2012/0201428 A1* | 8/2012 | Joshi | G06T 11/006 |
| | | | 382/107 |
| 2013/0182932 A1* | 7/2013 | Chen | G06T 11/008 |
| | | | 382/131 |
| 2013/0187649 A1 | 7/2013 | Bhat | |
| 2014/0012061 A1 | 1/2014 | Song | |
| 2014/0146936 A1 | 5/2014 | Liu | |
| 2018/0116596 A1* | 5/2018 | Sanders, III | A61B 6/037 |
| 2018/0140216 A1* | 5/2018 | Li | A61B 5/02 |
| 2019/0117317 A1* | 4/2019 | Abayazid | A61B 5/7267 |

OTHER PUBLICATIONS

European Patent Office (EPO), Communication (Extended European Search Report) dated Nov. 22, 2021, related European patent application No. 19770794.6, pp. 1-6, claims searched, pp. 7-9.

ISA/US, United States Patent and Trademark Office (USPTO), International Search Report and Written Opinion dated Jun. 10, 2019, related PCT international application No. PCT/US2019/023706, pp. 1-8, claims searched, pp. 9-14.

\* cited by examiner

APPARATUS AND METHOD FOR REMOVING BREATHING MOTION ARTIFACTS IN CT SCANS

CROSS-REFERENCE TO RELATED APPLICATIONS

This application claims priority to, and is a 35 U.S.C. § 111(a) continuation of, PCT international application number PCT/US2019/023706 filed on Mar. 22, 2019, incorporated herein by reference in its entirety, which claims priority to, and the benefit of, U.S. provisional patent application Ser. No. 62/646,968 filed on Mar. 23, 2018, incorporated herein by reference in its entirety. Priority is claimed to each of the foregoing applications.

The above-referenced PCT international application was published as PCT International Publication No. WO 2019/183562 A1 on Sep. 26, 2019, which publication is incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to medical imaging, and more particularly to medical imaging during patient motion.

2. Background Discussion

Accurate biomechanical modeling relies on accurate tissue deformation measurements, which themselves require artifact-free images. Patient-induced image motion blurring impacts all breathing CT scans of the thorax and upper abdomen. For radiation therapy, this degrades image quality and image registration accuracy. For pulmonology and upper abdomen imaging, this degrades the ability to use the scan for diagnosis or treatment response monitoring.

In pulmonology and upper abdominal imaging, the existing state of the art is to make Computed Tomography (CT) scanners faster, but they have reached their practical limit. With modern CT scanners, fast helical free breathing CT scans can be conducted extremely quickly and the time imaging any one location in the patient is less than 0.3 s. While this short amount of time reduces motion-induced image artifacts, it does not eliminate the artifacts. In cardiac imaging, motion modeling is generally integrated into the image reconstruction process. While, cardiac imaging may take advantage of the regularity of the cardiac cycle, the breathing cycle can be very irregular, so these techniques do not work when removing motion artifacts from lung or upper abdomen imaging.

Accordingly, modern CT-based pulmonology research relies on breath-hold CT, i.e. where the patient is asked to hold their breath. However, there are some circumstances when this is neither possible nor desired. Some patients are unable to hold their breath, whether due to lung disease or inability to understand or follow breath hold instructions.

There are also some imaging studies that are intended to measure or evaluate the patient under free breathing or other conditions, so holding their breath is undesirable, as breath-hold CT removes or eliminates any ability to measure dynamically relevant features of breathing.

There are no existing methods for reducing motion blurring except breath hold. This is impractical for some patients and limits the diagnostic information for pulmonology and upper abdominal imaging applications.

BRIEF SUMMARY

One aspect of the present disclosure is a method and apparatus for removing breathing motion artifacts in imaging CT scans by, for example, (i) acquiring raw imaging data from a CT scanner as an input; (ii) processing the raw CT imaging data by removing motion-induced artifacts; and (iii) outputting an artifact-free image; (iv) wherein processing the raw CT imaging data comprises initially estimating a 3D image to provide an estimate of raw sinogram image data, comparing the estimate to an actual CT sinogram, determining a difference between the sinograms, and iteratively reconstructing the 3D image by using the difference to alter the 3D image until the sinograms agree; and (v) wherein the 3D image moves according to a predetermined motion model.

The systems and methods of the present technology use an iterative process to produce a CT scan image of a free-breathing patient with the spatial resolution as though the patient had held their breath.

While the systems and methods disclosed herein are depicted and detailed with respect to removing breathing motion artifacts for CT imaging, it is appreciated that the systems and methods may be used for removing any motion artifact (e.g. from other patient musculature) in any number of imaging modalities (e.g. MRI, ultrasound, etc.)

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Modern CT scanners acquire images very quickly, moving the patient as the CT scanner rotates. This is termed helical scanning and is used for most CT scanning image acquisition. Breathing motion induces artifacts and blurring in the images that can degrade the diagnostic utility of the images. Under breathing conditions, standard helical CT reconstruction yields artifacts. In contrast to traditional iterative approaches, the 3D image in the methods disclosed herein is not static during the time represented by the CT scan acquisition.

Figure 1:
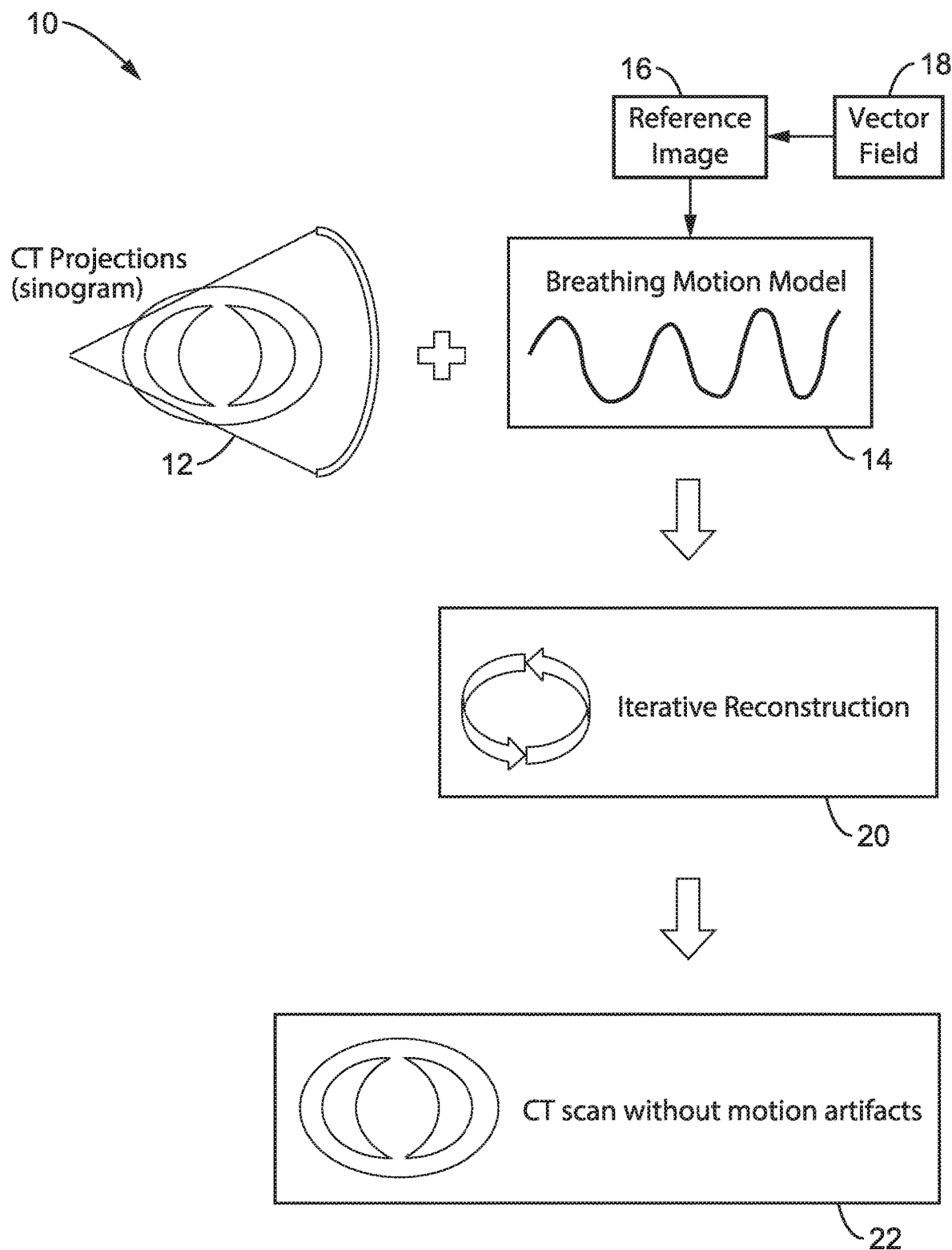
FIG. 1 shows a schematic process flow diagram of a first embodiment of the presented technology in which the target anatomy of the 3D image to be reconstructed is not static and moves during the time of the imaging scan acquisition.

FIG. 1 shows a schematic process flow diagram of a first imaging method 10 for 3D imaging of non-static target subject matter to create a static 3D image without breathing motion artifacts. CT projections (sinograms) 12 are acquired from the CT scanner as a series of frames. Method 10 employs a motion model estimation 14 along with the CT projection 12 (the raw sinogram data used by CT scanners to reconstruct the image) to the image reconstruction process. In this method, the generated 3D image will move according to the predetermined breathing motion model 14. In a preferred embodiment, the motion estimation model uses a reference image 16. The reference image 16 may comprise a 3D image that can be a previously acquired CT scan, a CT scan reconstructed from a previous iteration, or other source of 3D image. The reference image 16 is representative of the patient's tissue geometry at a specific breathing phase, for example at exhalation. An iterative reconstruction 20 is then employed with the motion model 14 to generate a CT scan 22 without motion artifacts.

Figure 2:
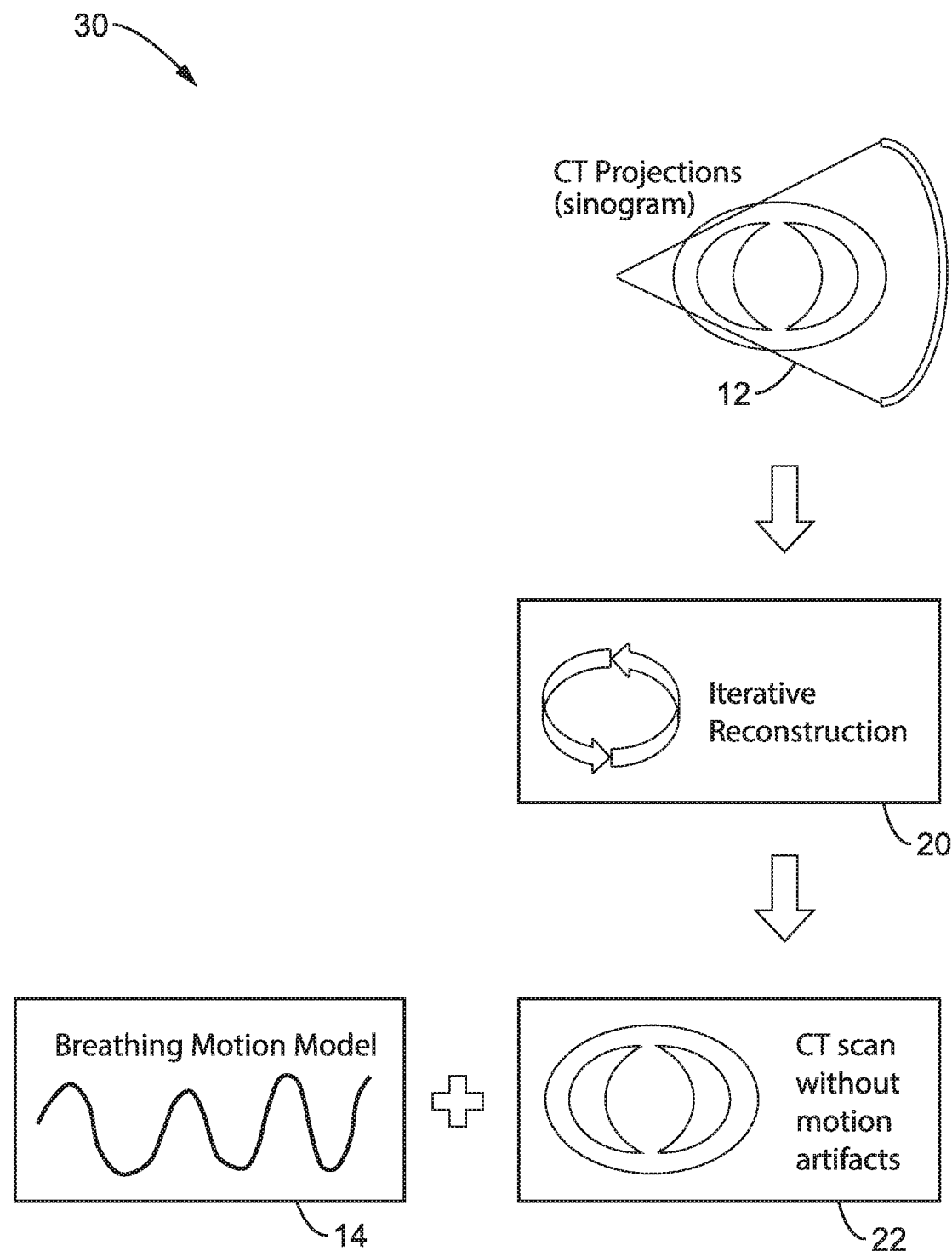
FIG. 2 shows a schematic process flow diagram of a second embodiment of the presented technology in which the reconstructed 3D image is not static and moves according to a motion model determined as part of the iterative reconstruction process.

FIG. 2 shows a method 30, the motion model 14 is determined as part of the iterative reconstruction step 20 with the acquired sinograms 12 to generate a CT scan 22 without motion artifacts. In method 30, the iterative reconstruction step 20 creates both an image without breathing motion artifacts 22 and simultaneously a breathing motion model 14. Both the model 14 and the image 22 are iterated such that a final quality metric, such as image sharpness, is optimized. As the motion model 14 is improved, the iterated images will get sharper and sharper, with reductions in motion artifacts, until no more improvement can be made. At that point, the breathing motion used in the iteration will be the breathing motion model 14.

Figure 3:
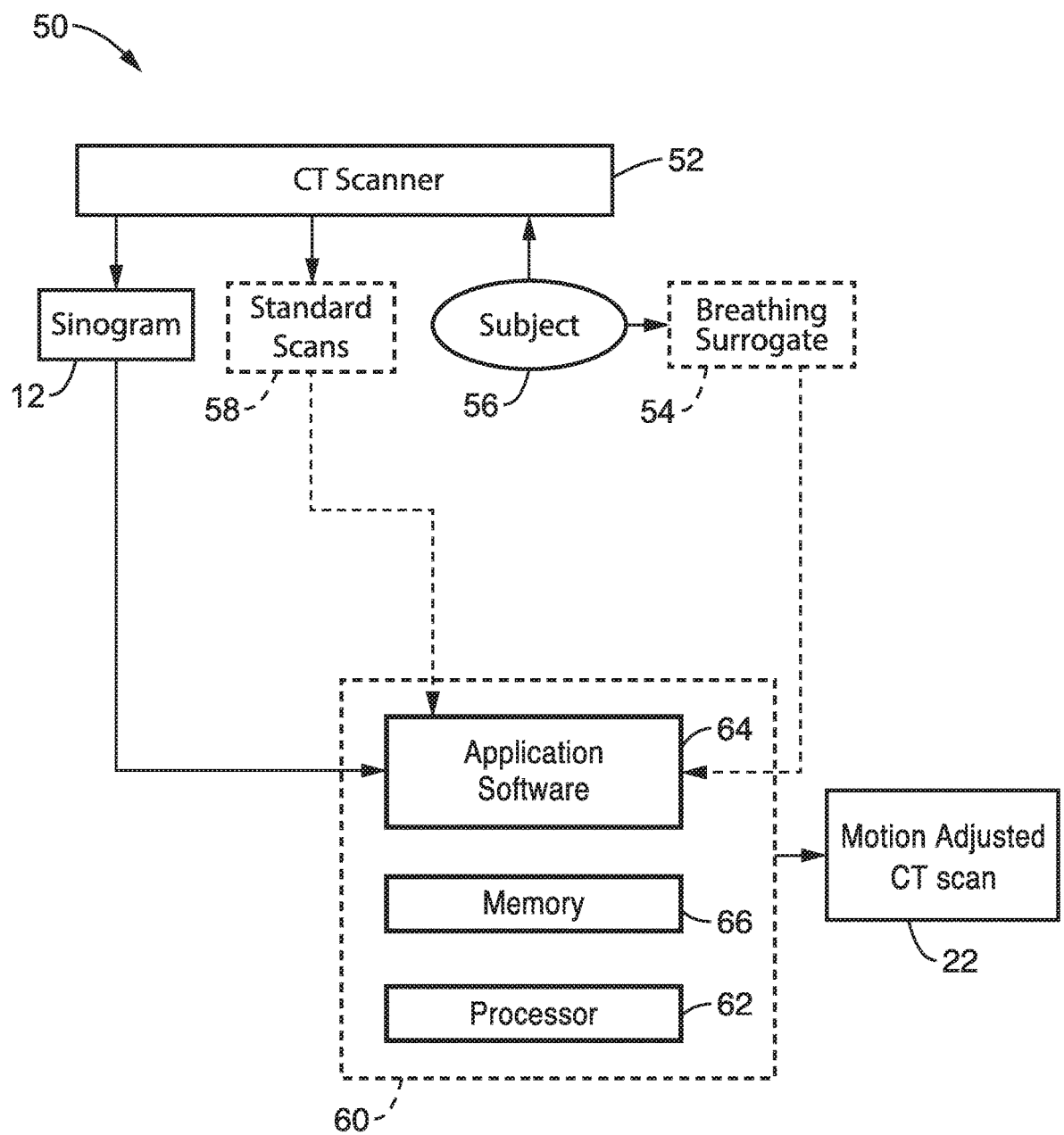
FIG. 3 shows a schematic system diagram for removing motion artifacts using the methods of the presented technology.

FIG. 3, shows schematic diagram of a system 50 for removing motion artifacts using either of the methods of FIG. 1 or FIG. 2. System 50 acquires the CT projections (series of sinogram frames) 12 of the subject (e.g. patient) 56 via CT scanner 52. The acquired sinograms 12 are used to reconstruct the 3D image of the target anatomy 56.

In one embodiment, one or more breathing motion surrogates 54 are input. Alternatively, the motion breathing model 14 may be generated from the image data itself, e.g. the standard (original) CT images 58 or data relating to time, CT gantry angle, etc. The breathing surrogate 54 may be simultaneously integrated along with the raw sinogram data 12 and the breathing motion model 14 to create motion artifact-reduced or eliminated images. The one or more breathing surrogates 54 may comprise an image from an external noninvasive system such as a spirometer or abdominal belt, camera-based system, or the like.

A computer 60 may be used to process the acquired CT and reference data according to application programming 64, which may comprise instructions that are stored in memory 66 and executable on processor 62 to employ the methods 10/30 for generated the motion-artifact removal described herein.

In a preferred embodiment, the motion model estimation 14 and image reconstruction 20 processes are conducted in an interleaved fashion, typically alternating between the two until an adequate image quality is reached.

In one embodiment, application programming 64 is configured such that the motion model 14 is generated earlier or in a previous process iteration and coupled to the breathing motion surrogate 54, which generally comprises a measured quantity that is quantitatively connected to the breathing phase, for example spirometry-measured tidal volume. In another embodiment, the motion model 14 is related to time or CT gantry angle.

Application programming 64 may employ a conventional iterative reconstruction method that applies the motion model 14 to the iterated image using motion that is consistent with the sinogram acquisition time and subsequent surrogate value when appropriate. Examples of suitable iterative reconstruction methods include, but are limited to, the SART method (see, for example, Andersen and Kak, "Simultaneous algebraic reconstruction technique (SART): A superior implementation of the ART algorithm", Ultrasonic Imaging, 6, 81-94 (1984)) incorporated herein by reference. For CT reconstruction, the image is reconstructed such that in each iteration, projections are cast through the current image iteration, compared against the measured sinogram data, and their differences cast back projected through the image to act as improvements to the reconstructed image.

In one embodiment, the method 10 employs a breathing motion model that is iteratively developed or updated by the motion estimation process. A reference image 16 is employed that is previously acquired or the output of a previous image-reconstruction iteration. The motion model 14 is updated using the CT sinogram data 12, typically one sinogram frame at a time. The reference image 16 is deformed using a vector field 18 that is computed using the motion model consistent with the time the sinogram frame was acquired (see FIG. 1). This vector field 18 is called the previous model iteration generated vector field. Image projections are calculated through the deformed image to the detector plane, forming a calculated sinogram frame. The calculated sinogram frame may be compared against the measured sinogram frame using rigid or deformable image registration. The registration vectors, termed error vectors, are back projected through the patient geometry. The projected error vectors are added to the previous model iteration generated vector field. These vectors are in turn used to regenerate the next iteration of the motion model. The process is repeated at the next sinogram frame, where the order of the analyzed sinogram frames may be in order of acquisition time, breathing surrogate value, or other order. The motion model estimation process 14 is finalized when the calculated sinogram frames are sufficiently similar to the measured sinogram frames according to a predetermined criterion.

The motion model 14 may be published or unpublished and is means for connecting the sinogram data to each other via a surrogate, time, or CT gantry angle, in such a way as to allow an image to be formed that has greatly reduced or no breathing motion artifacts.

The motion model 14 may be taken as a prior (defined earlier), iteratively generated in the image process, or taken as a prior and modified in the image generation process. The motion model 14 can also be an output of the image generation process.

Rather than conducting traditional back projection, the systems and methods of the present technology employ iterative reconstruction. In one embodiment, an initial estimate of the 3D image is used and projected through to provide an estimate of the raw sinogram image data. That estimate is then compared against the actual CT sinogram to determine a difference, and the difference is then used to alter the 3D image until the sinograms agree.

Each of the foregoing embodiments utilizes an iterative process to produce a CT scan image of a free-breathing patient with the spatial resolution as though the patient had held their breath.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general-purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula (e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that the present disclosure encompasses multiple embodiments which include, but are not limited to, the following:

1. An apparatus for removing motion-induced artifacts in a scanned image, the apparatus comprising: (a) a computer processor; and (b) a non-transitory computer-readable memory storing instructions executable by the computer processor; (c) wherein said instructions, when executed by the computer processor, perform steps comprising: (i) acquiring raw imaging data of a moving target anatomy from an image scanner; (ii) generating a reference image representative of the target anatomy geometry at a specific phase of motion; (iii) generating a motion model as a function of the reference image; (iv) iteratively reconstructing a 3D image of the target anatomy with the motion model to remove motion-induced artifacts from the image; and (v) outputting a motion artifact-free 3D image.

2. The apparatus or method of any preceding or subsequent embodiment, wherein the 3D image moves according to the motion model.

3. The apparatus or method of any preceding or subsequent embodiment, wherein the motion-induced artifacts comprise breathing motion of the target anatomy, and wherein the image is representative of the target anatomy at a specific breathing phase.

4. The apparatus or method of any preceding or subsequent embodiment, wherein the raw imaging data comprises a computed tomography (CT) sinograms acquired as a series of frames.

5. The apparatus or method of any preceding or subsequent embodiment, wherein the reference image of the target anatomy is generated from one or more of: a previously acquired imaging scan or sinogram, an imaging scan reconstructed from a previous scan iteration, or a 3D image acquired from another source.

6. The apparatus or method of any preceding or subsequent embodiment: (vi) wherein generating a reference image comprises estimating a reference 3D image to provide an estimate of the acquired sinogram image data; and (vii) wherein iteratively reconstructing a 3D image comprises comparing the estimate to an acquired sinogram and determining a difference between the reference 3D image and the acquired sinogram, and iteratively reconstructing the 3D image by using the determined difference to alter the 3D image until the reference 3D image and the acquired sinogram agree.

7. The apparatus or method of any preceding or subsequent embodiment, wherein the motion model is generated via a breathing motion surrogate that is quantitatively coupled to the breathing phase.

8. The apparatus or method of any preceding or subsequent embodiment, wherein the breathing motion surrogate is a function of one or more of spirometry-measured tidal volume or CT gantry angle.

9. The apparatus or method of any preceding or subsequent embodiment, wherein the breathing motion surrogate comprises an image acquired from an external noninvasive device.

10. The apparatus or method of any preceding or subsequent embodiment, wherein the 3D image is reconstructed such that in each iteration, one or more projections are cast through a current image iteration and compared against measured sinogram data, wherein differences between the current image iteration and measured sinogram data are cast back-projected through the 3D image to improve the 3D image.

11. A system for removing breathing motion artifacts in CT scans, the system comprising: (a) a CT scanner; (b) a computer processor; and (c) a non-transitory computer-readable memory storing instructions executable by the computer processor; (d) wherein said instructions, when executed by the computer processor, perform steps comprising: (i) acquiring raw imaging data of a moving target anatomy from the CT scanner, the raw imaging data comprising sinograms acquired as a series of frames; (ii) generating a reference image representative of the target anatomy geometry at a specific phase of motion; (iii) generating a motion model as a function of the reference image; (iv) iteratively reconstructing a 3D image of the target anatomy with the motion model to remove motion-induced artifacts from the image; and (v) outputting a motion artifact-free 3D image.

12. The apparatus or method of any preceding or subsequent embodiment, wherein the 3D image moves according to the motion model.

13. The apparatus or method of any preceding or subsequent embodiment, wherein the motion-induced artifacts comprise breathing motion of the target anatomy, and wherein the image is representative of the target anatomy at a specific breathing phase.

14. The apparatus or method of any preceding or subsequent embodiment, wherein the reference image of the target anatomy is generated from one or more of: a previously acquired imaging scan or sinogram, an imaging scan reconstructed from a previous scan iteration, or a 3D image acquired from another source.

15. The apparatus or method of any preceding or subsequent embodiment: (vi) wherein generating a reference image comprises estimating a reference 3D image to provide an estimate of the acquired sinogram image data; and (vii) wherein iteratively reconstructing a 3D image comprises comparing the estimate to an acquired sinogram and determining a difference between the reference 3D image and the acquired sinogram, and iteratively reconstructing the 3D image by using the determined difference to alter the 3D image until the reference 3D image and the acquired sinogram agree.

16. The apparatus or method of any preceding or subsequent embodiment, wherein the motion model is generated via a breathing motion surrogate that is quantitatively coupled to the breathing phase.

17. The apparatus or method of any preceding or subsequent embodiment, wherein the breathing motion surrogate is a function of one or more of spirometry-measured tidal volume or CT gantry angle.

18. The apparatus or method of any preceding or subsequent embodiment, wherein the breathing motion surrogate comprises an image acquired from an external noninvasive device.

19. The apparatus or method of any preceding or subsequent embodiment, wherein the 3D image is reconstructed such that in each iteration, one or more projections are cast through a current image iteration and compared against measured sinogram data, wherein differences between the current image iteration and measured sinogram data are cast back-projected through the 3D image to improve the 3D image.

20. A computer implemented method for removing motion-induced artifacts in a scanned image, the method comprising: (a) acquiring raw imaging data of a moving target anatomy from an image scanner; (b) generating a reference image representative of the target anatomy geometry at a specific phase of motion; (c) generating a motion model as a function of the reference image; (d) iteratively reconstructing a 3D image of the target anatomy with the motion model to remove motion-induced artifacts from the image; and (e) outputting a motion artifact-free 3D image; (f) wherein said method is performed by a computer processor executing instructions stored on a non-transitory computer-readable medium.

21. The apparatus or method of any preceding or subsequent embodiment, wherein the 3D image moves according to the motion model.

22. The apparatus or method of any preceding or subsequent embodiment, wherein the motion-induced artifacts comprise breathing motion of the target anatomy, and wherein the image is representative of the target anatomy at a specific breathing phase.

23. The apparatus or method of any preceding or subsequent embodiment, wherein the raw imaging data comprises a computed tomography (CT) sinograms acquired as a series of frames.

24. The apparatus or method of any preceding or subsequent embodiment, wherein the reference image of the target anatomy is generated from one or more of: a previously acquired imaging scan or sinogram, an imaging scan reconstructed from a previous scan iteration, or a 3D image acquired from another source.

25. The apparatus or method of any preceding or subsequent embodiment: (g) wherein generating a reference image comprises estimating a reference 3D image to provide an estimate of the acquired sinogram image data; and (h) wherein iteratively reconstructing a 3D image comprises comparing the estimate to an acquired sinogram and determining a difference between the reference 3D image and the acquired sinogram, and iteratively reconstructing the 3D image by using the determined difference to alter the 3D image until the reference 3D image and the acquired sinogram agree.

26. The apparatus or method of any preceding or subsequent embodiment, wherein the motion model is generated via a breathing motion surrogate that is quantitatively coupled to the breathing phase.

27. The apparatus or method of any preceding or subsequent embodiment, wherein the breathing motion surrogate is a function of one or more of spirometry-measured tidal volume or CT gantry angle.

28. The apparatus or method of any preceding or subsequent embodiment, wherein the breathing motion surrogate comprises an image acquired from an external noninvasive device.

29. The apparatus or method of any preceding or subsequent embodiment, wherein the 3D image is reconstructed such that in each iteration, one or more projections are cast through a current image iteration and compared against measured sinogram data, wherein differences between the current image iteration and measured sinogram data are cast back-projected through the 3D image to improve the 3D image.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for removing motion-induced artifacts in a scanned image, the apparatus comprising:
   (a) a computer processor; and
   (b) a non-transitory computer-readable memory storing instructions executable by the computer processor;
   (c) wherein said instructions, when executed by the computer processor, perform steps comprising:
      (i) acquiring raw imaging data of a moving target anatomy from an image scanner;
      (ii) generating a reference image representative of the target anatomy geometry at a specific phase of motion;
      (iii) generating a motion model as a function of the reference image;
      (iv) iteratively reconstructing a 3D image of the target anatomy with the motion model to remove motion-induced artifacts from the image; and
      (v) outputting a motion artifact-free 3D image.

2. The apparatus of claim 1, wherein the 3D image moves according to the motion model.

3. The apparatus of claim 1, wherein the motion-induced artifacts comprise breathing motion of the target anatomy, and wherein the image is representative of the target anatomy at a specific breathing phase.

4. The apparatus of claim 3, wherein the raw imaging data comprises a computed tomography (CT) sinograms acquired as a series of frames.

5. The apparatus of claim 4, wherein the reference image of the target anatomy is generated from one or more of: a previously acquired imaging scan or sinogram, an imaging scan reconstructed from a previous scan iteration, or a 3D image acquired from another source.

6. The apparatus of claim 4:
   (vi) wherein generating a reference image comprises estimating a reference 3D image to provide an estimate of the acquired sinogram image data; and
   (vii) wherein iteratively reconstructing a 3D image comprises comparing the estimate to an acquired sinogram and determining a difference between the reference 3D image and the acquired sinogram, and iteratively reconstructing the 3D image by using the determined difference to alter the 3D image until the reference 3D image and the acquired sinogram agree.

7. The apparatus of claim 4, wherein the motion model is generated via a breathing motion surrogate that is quantitatively coupled to the breathing phase.

8. The apparatus of claim 7, wherein the breathing motion surrogate is a function of one or more of spirometry-measured tidal volume or CT gantry angle.

9. The apparatus of claim 7, wherein the breathing motion surrogate comprises an image acquired from an external noninvasive device.

10. The apparatus of claim 6, wherein the 3D image is reconstructed such that in each iteration, one or more projections are cast through a current image iteration and compared against measured sinogram data, wherein differences between the current image iteration and measured sinogram data are cast back-projected through the 3D image to improve the 3D image.

11. A system for removing breathing motion artifacts in CT scans, the system comprising:
(a) a CT scanner;
(b) a computer processor; and
(c) a non-transitory computer-readable memory storing instructions executable by the computer processor;
(d) wherein said instructions, when executed by the computer processor, perform steps comprising:
(i) acquiring raw imaging data of a moving target anatomy from the CT scanner, the raw imaging data comprising sinograms acquired as a series of frames;
(ii) generating a reference image representative of the target anatomy geometry at a specific phase of motion;
(iii) generating a motion model as a function of the reference image;
(iv) iteratively reconstructing a 3D image of the target anatomy with the motion model to remove motion-induced artifacts from the image; and
(v) outputting a motion artifact-free 3D image.

12. The system of claim 11, wherein the 3D image moves according to the motion model.

13. The system of claim 11, wherein the motion-induced artifacts comprise breathing motion of the target anatomy, and wherein the image is representative of the target anatomy at a specific breathing phase.

14. The system of claim 11, wherein the reference image of the target anatomy is generated from one or more of: a previously acquired imaging scan or sinogram, an imaging scan reconstructed from a previous scan iteration, or a 3D image acquired from another source.

15. The system of claim 13:
(vi) wherein generating a reference image comprises estimating a reference 3D image to provide an estimate of the acquired sinogram image data; and
(vii) wherein iteratively reconstructing a 3D image comprises comparing the estimate to an acquired sinogram and determining a difference between the reference 3D image and the acquired sinogram, and iteratively reconstructing the 3D image by using the determined difference to alter the 3D image until the reference 3D image and the acquired sinogram agree.

16. The system of claim 13, wherein the motion model is generated via a breathing motion surrogate that is quantitatively coupled to the breathing phase.

17. The system of claim 16, wherein the breathing motion surrogate is a function of one or more of spirometry-measured tidal volume or CT gantry angle.

18. The system of claim 16, wherein the breathing motion surrogate comprises an image acquired from an external noninvasive device.

19. The system of claim 15, wherein the 3D image is reconstructed such that in each iteration, one or more projections are cast through a current image iteration and compared against measured sinogram data, wherein differences between the current image iteration and measured sinogram data are cast back-projected through the 3D image to improve the 3D image.

20. A computer implemented method for removing motion-induced artifacts in a scanned image, the method comprising:
(a) acquiring raw imaging data of a moving target anatomy from an image scanner;
(b) generating a reference image representative of the target anatomy geometry at a specific phase of motion;
(c) generating a motion model as a function of the reference image;
(d) iteratively reconstructing a 3D image of the target anatomy with the motion model to remove motion-induced artifacts from the image; and
(e) outputting a motion artifact-free 3D image;
(f) wherein said method is performed by a computer processor executing instructions stored on a non-transitory computer-readable medium.

21. The method of claim 20, wherein the 3D image moves according to the motion model.

22. The method of claim 20, wherein the motion-induced artifacts comprise breathing motion of the target anatomy, and wherein the image is representative of the target anatomy at a specific breathing phase.

23. The method of claim 22, wherein the raw imaging data comprises a computed tomography (CT) sinograms acquired as a series of frames.

24. The method of claim 23, wherein the reference image of the target anatomy is generated from one or more of: a previously acquired imaging scan or sinogram, an imaging scan reconstructed from a previous scan iteration, or a 3D image acquired from another source.

25. The method of claim 20:
(g) wherein generating a reference image comprises estimating a reference 3D image to provide an estimate of the acquired sinogram image data; and
(h) wherein iteratively reconstructing a 3D image comprises comparing the estimate to an acquired sinogram and determining a difference between the reference 3D image and the acquired sinogram, and iteratively reconstructing the 3D image by using the determined difference to alter the 3D image until the reference 3D image and the acquired sinogram agree.

26. The method of claim 23, wherein the motion model is generated via a breathing motion surrogate that is quantitatively coupled to the breathing phase.

27. The method of claim 26, wherein the breathing motion surrogate is a function of one or more of spirometry-measured tidal volume or CT gantry angle.

28. The method of claim 26, wherein the breathing motion surrogate comprises an image acquired from an external noninvasive device.

29. The method of claim 25, wherein the 3D image is reconstructed such that in each iteration, one or more projections are cast through a current image iteration and compared against measured sinogram data, wherein differences between the current image iteration and measured sinogram data are cast back-projected through the 3D image to improve the 3D image.

* * * * *